(12) United States Patent
Anquez et al.

(10) Patent No.: US 12,285,637 B2
(45) Date of Patent: Apr. 29, 2025

(54) METHOD AND DEVICE FOR TREATING VARICOSE VEINS BY APPLICATION OF HIGH-INTENSITY FOCUSED ULTRASOUND

(71) Applicant: THERACLION SA, Malakoff (FR)

(72) Inventors: Jérémie Anquez, Paris (FR); Anthony Grisey, Saint Cyr l'Ecole (FR); Michel Nuta, Gentilly (FR)

(73) Assignee: THERACLION SA, Malakoff (FR)

( * ) Notice: Subject to any disclaimer, the term of this patent is extended or adjusted under 35 U.S.C. 154(b) by 178 days.

(21) Appl. No.: 17/619,509

(22) PCT Filed: Jun. 17, 2020

(86) PCT No.: PCT/EP2020/066773
§ 371 (c)(1),
(2) Date: Dec. 15, 2021

(87) PCT Pub. No.: WO2020/254412
PCT Pub. Date: Dec. 24, 2020

(65) Prior Publication Data
US 2022/0226673 A1    Jul. 21, 2022

(30) Foreign Application Priority Data
Jun. 19, 2019    (WO) .................. PCT/IB2019/000678

(51) Int. Cl.
*A61N 7/02*    (2006.01)
*A61N 7/00*    (2006.01)

(52) U.S. Cl.
CPC ........ *A61N 7/02* (2013.01); *A61N 2007/0004* (2013.01)

(58) Field of Classification Search
CPC .. A61N 7/02; A61N 2007/0004; A61N 18/04; A61B 18/04
See application file for complete search history.

(56) References Cited

U.S. PATENT DOCUMENTS

| 10,231,712 B2 | 3/2019 | Ebbini et al. | |
| 2007/0088346 A1* | 4/2007 | Mirizzi .................... | A61N 7/02 606/27 |

(Continued)

FOREIGN PATENT DOCUMENTS

| WO | 20080144274 A2 | 11/2008 |
| WO | 2020254412 A1 | 12/2020 |

OTHER PUBLICATIONS

"Partial shrinkage of venous tissues near values using High Intensity Focused Ultrasound" by S. Pichardo et al. AIP Conf. Proc. 754. pp. 264-268. (Year: 2005).*

(Continued)

*Primary Examiner* — Jason M Ip
(74) *Attorney, Agent, or Firm* — Finch & Maloney PLLC (57) ABSTRACT

The invention is directed to a method of non-invasively treating a varicose vein (2), for example the Great saphenous vein (GSV), wherein the vein or the vein system to be treated is divided into sections (6a, 6b, 6c, 6d) with a length (11) separated by a spacing (s1). The sections can be pre-defined before the treatment, for example to target a junction (4) to a tributary (3), or with respect to the sapheno-femoral junction (8), and can vary in length and location, for example to avoid a sensitive structure (7) such as nerves.

27 Claims, 5 Drawing Sheets

(56) References Cited

U.S. PATENT DOCUMENTS

| | | | |
|---|---|---|---|
| 2009/0036773 A1* | 2/2009 | Lau ........................ | A61B 8/445 |
| | | | 600/439 |
| 2010/0160781 A1* | 6/2010 | Carter ...................... | A61B 8/06 |
| | | | 600/439 |
| 2010/0256534 A1 | 10/2010 | Lacoste et al. | |
| 2010/0274161 A1 | 10/2010 | Azhari et al. | |
| 2013/0190661 A1 | 7/2013 | Wing et al. | |
| 2022/0175357 A1* | 6/2022 | Ding ........................ | A61N 7/02 |

OTHER PUBLICATIONS

International Search Report and the Written Opinion of the International Searching Authority for International Application No. PCT/EP2020/066773 mailed Aug. 21, 2020, 19 pages.

\* cited by examiner

METHOD AND DEVICE FOR TREATING VARICOSE VEINS BY APPLICATION OF HIGH-INTENSITY FOCUSED ULTRASOUND

The present invention relates to a method of treating varicose veins by application of High-Intensity Focused Ultrasound (HIFU) comprising the features of the independent claim.

HIFU treatments enable the non-invasive ablation of anatomical targets in the body. They are usually guided based on an imaging modality such as ultrasonography, in particular B-mode imaging.

In several devices, an ultrasonography imaging transducer is embedded in the "treatment head" subsystem which also comprises a therapy transducer as described e.g. in WO 2006/129045.

For treating varicose veins, it is known to use Radio Frequency Ablations (RFA) or Endovenous Laser Ablations (EVLA). These procedures generally rely on treating the vein from the sapheno-femoral junction (with a safety distance of a few centimetres) up to the knee or the ankle.

Treating such a length with HIFU may take a long time. HIFU is therefore sometimes considered less suitable for treatment of varicose veins. Indeed, HIFU treatments generally require pauses between the pulses, for example to avoid skin burns, which can lead to treatment durations exceeding an hour for long veins such as the Great Saphenous Vein (GSV). In addition, the supply of energy to the vein system can be painful for a patient. Thus, current HIFU treatments of vein systems can cause severe discomfort for the treated patient.

It is known in the prior art to treat varicose veins by closing parts of veins with the goal of selectively changing the blood flow. This method, commonly referred to as CHIVA method, requires anesthesia and involves surgical treatment of the leg and the varicose veins.

It is the object of the present invention to overcome the disadvantages of the prior art, in particular to provide a method which allows to non-invasively treat a vein with HIFU and in particular avoid a time-consuming treatment and pain, stress and discomfort for the patient.

This and other objects are solved by the present invention and the method according to independent claim.

As will be clear to a person skilled in the art, the treatment described herein can of course be combined with other treatment methods. As such, any description herein should not be understood as a limitation to a treatment exclusively with HIFU.

In the method according to the invention, first, at least one first section of the vein to be treated is identified. A first section is treated by applying HIFU emitted from a treatment head to the first section. An area neighbouring the section is not treated with HIFU. In other words, the method according to the invention is based on performing a sectional treatment. It has been surprisingly found that it is not necessary to treat the vein along its entire length but that the treatment of at least one section is sufficient. Typically, the treatment can occur in only one section but also in a plurality of sections (e.g. at least two sections) spaced from each other along the vein.

A section in the context of the present invention means a part of a vein, in particular a part of a vein within a single vein system. Herein, vein system refers to the vein to be treated and every vein directly connected to the vein to be treated, in particular every vein directly connected to the vein to be treated in an upstream direction. Unless otherwise indicated and/or specified, a plurality of sections shall refer to sections within the same vein system. A section can refer to a portion of a vein or a vein system representing a percentage of said vein or vein system. It can also refer to a portion of a vein or vein system with a defined total length. A section can also generically refer to a portion of a vein or a vein system that is adjacent to at least one other portion of the same vein or vein system that was treated differently from the section.

Preferably, the at least one section is part of segment of the vein that is non-functional. At least a second section of the segment may not be treated with HIFU. The treated section is preferably completely occluded.

Methods known in the prior art typically identify veins, vein systems, or more generally non-functional segments of vein systems that have lost their healthy functionality. For example, a portion of a varicose vein may be dilated and the valves can no longer stop backflow of blood. Such segments are then treated in their entirety. If a HIFU treatment were envisioned, for example, methods known in the art would treat the entire segment with HIFU.

By contrast, the method according to the invention may preferably be used to only treat a section of such a segment. Particularly preferably, at least two sections of a continuous non-healthy segment are treated, wherein the at least two sections are separated by a section that is not treated. It is also possible to only treat one section of a segment.

The treated section may be adjacent to a healthy, functional segment of a vein. Alternatively, the section may be located within the non-functional segment such as to be adjacent to non-healthy, non-functional vein parts.

In a preferred variant of the method according to the invention, the treated section is completely occluded. In particular, the power of a HIFU pulse, the duration of the treatment, and the number of pulses may be chosen such as to completely occlude the treated section.

Thus, the method particularly preferably includes a step of identifying a section to be treated, wherein the section is part of a non-healthy, non-functional segment. A length of the section, measured along the longitudinal axis of the vein, is shorter than the length of the segment.

The method may also include a step of occluding the section completely.

In the context of the present application, a section is typically, but not necessarily, a section of the vein or a vein segment which has a length of less than 200 mm and/or 50% of the total length of the vein or vein segment.

In particular, unless otherwise indicated and/or specified, treating a section refers to treating at least 50% for a circumference of at least one layer of a vein wall. For example, it can refer to treating 50% of a circumference of the tunica intima, the tunica media, and/or the tunica adventitia.

In particular, a section can be a portion of a vein or a vein system that is to be treated by HIFU and is adjacent to a portion that is not to be treated by HIFU, or is to be treated with substantially different treatment characteristics (for example, power, pulse duration, and/or frequency). Substantially different treatment characteristics shall denominate differences greater than a standard deviation, in particular greater than normal fluctuations caused by precision limits of a device. Additionally or alternatively, substantially different treatment characteristics shall include characteristics that do not cause a treatment effect.

For example, in a first section, three or four pulses are delivered in all treated cross-sections, resulting in a mean of 3.5 pulses delivered per cross-section and a standard deviation of 0.2 pulses in this section, while, in the second section, only two pulses are delivered in all treated cross-sections, which is smaller than the mean (3.5) minus the standard deviation (0.2) and/or differences in the parameters inducing different significantly different biological effects (for example, thermal ablation versus mechanical ablation).

Furthermore, numbered sections, such as "first section", shall not denominate an order of treatment, but shall be used to identify different sections. For example, a second section may be treated before a first section. For example, the "first section" may refer to the most proximal section.

Distal, in the context of the present invention, shall refer to the direction opposite to the normal direction of flow in the vein and further away from the heart. Proximal shall refer to the normal direction of flow in the vein and closer to the heart.

The treated sections can be arranged depending on the specific vein which is treated. Typically, if the refluxing vein extends in the thigh and in the calf (e.g. the GSV), the sections are preferably mainly or only located in the thigh, since the sensitive structures are generally closer to the vein under the knee.

For example, in the case of a treatment of a GSV, one may begin the treatment at the sapheno-femoral junction.

If several tributaries are connected to the refluxing vein, the sectional approach described hereinabove can be adapted to account for the location of these tributaries. In this context, the tributary refers to a smaller vein that leads to a larger vein.

In particular, one and preferably multiple HIFU pulses can be emitted to the section to be treated. The HIFU pulses can be targeted at one spot or different spots within the same section.

The treatment head preferably comprises a conventional HIFU transducer or phased-array transducer.

In a preferred embodiment, the first section is treated without substantially moving the treatment head and/or the transducer. It is, however, also possible to move the head along the section during the treatment.

In a one embodiment of the present invention, only the first section is treated with HIFU.

In a preferred embodiment, the treatment step is repeated at least once for a second section distanced from the first section.

In preferred embodiment, the method is carried out to treat the GSV or the Anterior Accessory Saphenous Vein (AASV) as a refluxing vein. In this case, the first section begins close to the sapheno-femoral junction, preferably at a distance that is smaller than 2 cm.

In a preferred embodiment, the length of the treated section is greater than 5 cm, or greater than 10 cm.

In an alternative embodiment, the sum of the lengths of the treated sections is greater than 5 cm, preferably greater than 10 cm.

The length of the first section to be treated can in particular be chosen such as to not reach the level of the knee.

In an alternative preferred embodiment, the refluxing vein to be treated is a perforator vein. In this case the first section is located close to the fascia and preferably has a length smaller than 2 cm, or smaller than 1 cm.

In another preferred embodiment, the first section can be treated with different parameters than any other section. Typically, at least one of a.) the length of the treated section b.) the delivered energy, c.) the linear endovenous energy density, d.) the fluence, e.) the power, is substantially larger for the first, in particular the most proximal, section (which is preferably at a distance smaller than 2 cm from the sapheno-femoral junction, most preferably at the sapheno-femoral junction) than for at least one, preferably all, other sections.

In yet another preferred embodiment, at least one of the length and spacing of the sections is chosen such that sensitive surrounding structures that could be damaged by HIFU, for example nerves, possibly present along the vein are not subjected to HIFU.

In a preferred embodiment, the treated sections are spread all along the vein or the vein system, preferably in a regular pattern.

In an alternative preferred embodiment, the sections are arranged only in a predefined part of the vein or the vein system.

If the refluxing vein to be treated extends in the thigh and in the calf, the sections are located preferably mainly and more preferably only in the thigh.

In a preferred embodiment, the number, length, and/or location of the sections that are to be treated and/or a characteristic value of the Linear Endovenous Energy Density (LEED, W/cm) and/or the treatment power and/or the fluence, for each section is defined prior to the treatment, in particular prior to the emission of the first HIFU pulse. The characteristic value may be constant or may vary within a range. For example some characteristics of the sections can be defined based on a preliminary examination using ultrasound imaging.

In alternative preferred embodiment, the number, length, and/or location of the sections that are to be treated and/or a value of the LEED and/or the treatment power and/or the fluence for each section is adjusted or adjustable during the treatment, in particular after the first HIFU pulse has been emitted. For example, they can be adjusted based on the response of the vein to the treatment that may be determined by the presence or absence of flow in color Doppler).

In alternative preferred embodiment, at least one of the number, length and location of the sections is defined prior to the treatment, in particular after the first HIFU pulse has been emitted. Then, at least one of the number, length and location of the sections that are to be treated is adjusted or adjustable during the treatment, in particular, after the first HIFU pulse has been emitted. For example, for the treatment of a Great Saphenous Vein (GSV), based on the location of the tributaries (e.g. assessed by ultrasound imaging), it can be decided to place one section at the junction with at least one of the tributaries and one section at the Sapheno-Femoral junction. Then, during treatment, the length of the sections and/or a characteristic value of the LEED and/or of the power and/or of the fluence can be adjusted based on color Doppler information. For example, the length of the sections can be increased at least until no flow is visible in the section to be treated.

In a particularly preferred embodiment, the length of a treated section is reduced during the treatment if and when the vein becomes less visible due to heat-induced shrinkage of its wall. Preferably, in dependence of the reduced visibility of the vein, the treatment head is moved distally. At the new distal location, a new section is treated.

For example, if the vein becomes less visible, the treatment of the section can be aborted and a next section, in particular in a distal direction, is treated next.

Alternatively, if the vein becomes barely visible on the monitoring mean due to the heat-induced shrinkage of its wall, the treatment head is moved during the treatment, in particular along a direction parallel to the treated section, such that the treated vein or vein system is more easily visible. This process can be repeated until treatment completion.

For example, the vein may become barely visible during the treatment. Instead of continuing the current section, it may be decided to stop the treatment of the current segment, to move (e.g. more distally), and to deliver another section at this new location. Note that this second section was may be already planned (in this case, the first section is simply interrupted, but no other section is added). Alternatively, the second section was not planned. Alternatively, the second section was planned but some characteristics are changed due to this event (for example, its length is increased to compensate for the first section being shorter than expected).

In a preferred embodiment, the treatment is controlled or stopped on the basis of at least one of the level of total delivered energy, absence of detectable flow in the vein, treatment duration, total treated length, a predefined number of sections treated, and/or vein shrinkage. Typically, treatment will be stopped if certain treatment completion criteria defined by these parameters are fulfilled.

In a preferred embodiment, the sections are treated from the proximal side of the vein to the distal side of the vein. This is particularly advantageous if cavitation is used for achieving a treatment effect, since a proximal occlusion of the vein will block some blood distally and inflate the vein, thus letting enough blood to initiate cavitation.

Alternatively, especially if the vein is big and/or if only thermal pulses are used and/or if no tumescence is used, the treatment can start on the distal side to decrease the blood flow into the vein and to avoid the distal inflation. Alternatively, the order and direction of treatment of the sections are free.

In another preferred embodiment, at least one section is placed, in particular adapted in its length and position, to target a junction with a tributary.

In a preferred embodiment, the occlusion of the junctions includes one of i.) treating only the vein at said junction, ii.) treating the vein and the tributary at said junction, and iii.) treating only the tributary at the junction.

In another preferred embodiment, at least one tributary, in particular a tributary that is connected to the same vein, is treated away from the junction.

Additionally to a sectional HIFU treatment, an additional treatment with at least one other modality can be performed to treat at least part of the same vein system.

These modalities include, but are not limited to Radio Frequency Ablation, Endovenous Laser Ablation, Microwave ablation, heating with a hot catheter, mechanical damage of the endothelium, Glue, and/or Sclerotherapy or a combination of modalities. Preferably, Sclerotherapy is used to avoid the invasiveness related to the insertion of a catheter. Alternatively, the other treatment is performed with HIFU. In particular, the additional treatment is performed distally from the most proximal section treated with HIFU.

In a particularly preferred embodiment, the method according to the invention further comprises a step of treating the vein with sclerotherapy.

Sclerotherapy is a known treatment of varicose veins wherein a sclerosant is injected into a vein, causing occlusion of said vein. However, sclerosants may have undesired side effects and it is therefore advantageous if the treatment with a sclerosant can be as localized as possible.

To this end, a section of a non-healthy segment may be located at a downstream end of the segment, for example directly adjacent to a healthy, functional segment. Non-healthy segments may in particular not be able to properly prevent reflux of blood, i.e. flow of blood against the natural flow direction, which is one of the functions of veins. Downstream is understood here with respect to flow direction of blood. The section is occluded by means of HIFU. Subsequently, a sclerosant can be injected in the segment at an upstream position of the section. The occlusion of the section at the downstream end of the segment reduces or prevents passage of the sclerosant into the blood stream. Therefore, side effects of the sclerosants are reduced.

Preferred sclerosants are dodecylpolyethyleneglycolether (polidocanol), iodine, sodium tetradecyl sulfate, sodium salycilate, chromated glycerin and other ethers.

The other treatment, preferably sclerotherapy, can be performed during the same or another session, before or preferably after the HIFU treatment. Preferably, it targets at least part of the untreated part of the vein, most preferably the entire untreated part of the vein.

The additional treatment may be performed on a partially or totally occluded vein, in particular to avoid recanalisation. Partially occluded shall be understood as exhibiting signs of occlusion but still allowing for some blood flow.

Additionally or alternatively, it may also target some part of the vein(s) which was already treated by HIFU. In case sclerotherapy is used, it is preferably used when the vein is occluded to avoid the systemic (neurological etc.) side-effects related to the sclerosant being released in the blood circulation.

In another embodiment, at least one of the targeted veins is the Great Saphenous Vein or the Anterior Accessory Saphenous Vein and at least one section treated by HIFU is close to the Sapheno-Femoral Junction at the at least one additional treatment targets at least a more distal part of the vein.

Additionally or alternatively, the sum of all treatment delivered substantially corresponds to the length of the vein from the Sapheno-Femoral Junction to the level of the knee.

Additionally or alternatively, the sum of all treatments delivered substantially corresponds to the length of the vein from the Sapheno-Femoral Junction.

For example, it can be long to treat the whole Great Saphenous Vein with HIFU, thus, only one section is treated from the sapheno-femoral junction, but durability of the occlusion might not be as good as if the whole GSV would be treated. Thus, during a control session, preferably after the occlusion has been observed, a sclerotherapy is performed distally to the treated section to occlude at least some (preferably all) the distal part of the GSV.

The invention further relates to a device. The device according to the invention comprises a memory unit, a display, a control unit, and a treatment head with a transducer. The control unit is adapted to control the treatment head and the transducer, in particular such that different sections can be treated with different treatment characteristics, for example pulse length, number of pulses, power, LEED, fluence, length of the sections, number of sections, and/or others. Furthermore, the display is adapted to display the treatment characteristics for each section. In particular, the display may display the treatment characteristics as a table or as a graphic representation, for example with color codes overlaid over a B-mode image. The control unit is further adapted to compute characteristic values from the treatment characteristics, such as mean and median values. These values may be displayed on the display as well.

In the following, the present invention is described with reference to the figures and preferred embodiments, showing.

Figure 1A:
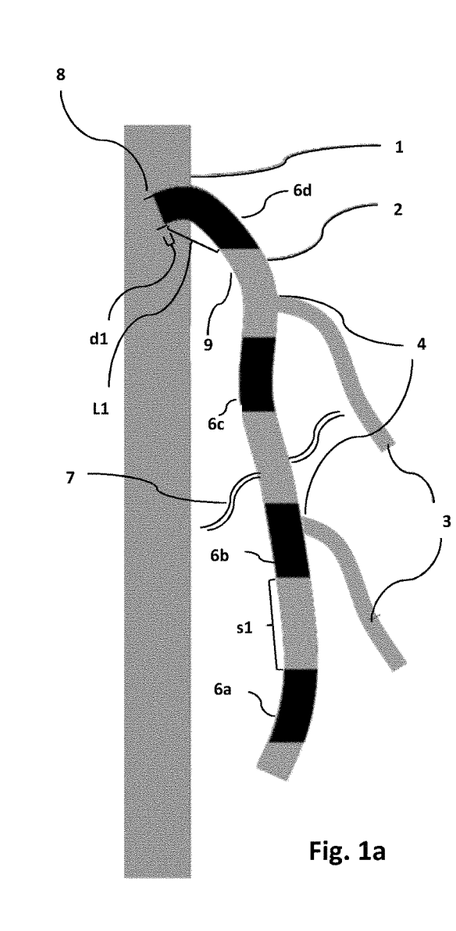
FIG. 1a: schematically the concept of a sectional treatment with several sections.

FIG. 1a shows schematically a method according to the invention, wherein several sections 6a, 6b, 6c, and 6d are treated along a vein system 1,2. Here, the refluxing vein 2 is the Great Saphenous Vein (GSV) or the Anterior Accessory Saphenous Vein (AASV) one treated section 6d begins as close as possible to the sapheno-femoral junction 8, preferably at a distance d1 smaller than 2 cm. The length L1 of the treated section 6d neighbouring the sapheno femoral junction 8 is bigger than the other treated sections. Alternatively, this section could also have the same size but the delivered energy could be higher, or the linear endovenous energy density could be higher than for the other sections 6a, 6b, and 6c. In the shown embodiment, the treated sections have equal spacings s1, but could also be of unequal spacing and/or lengths. In between the sections 6c and 6b, a nerve 7 is close to the refluxing vein 2. The position, length, and/or spacing of the treated sections is thus adjusted to avoid exposing and/or harming the nerve 7, which is a sensitive structure.

However, in the shown embodiment, the sections are not specifically arranged with respect to the junctions 4 between the tributaries 3 and the refluxing vein 2. Thus, one section 6b lies at a junction 4, while the other sections 6a, 6c, and 6d do not. The sections 6a, 6b, 6c, and 6d are spread equally along the treated vein 2. Here, the treatment is started with proximal section 6d, while an area neighboring the section 9 is not treated. Alternatively, the treatment can be started with a distal section 6a.

Figure 1B:
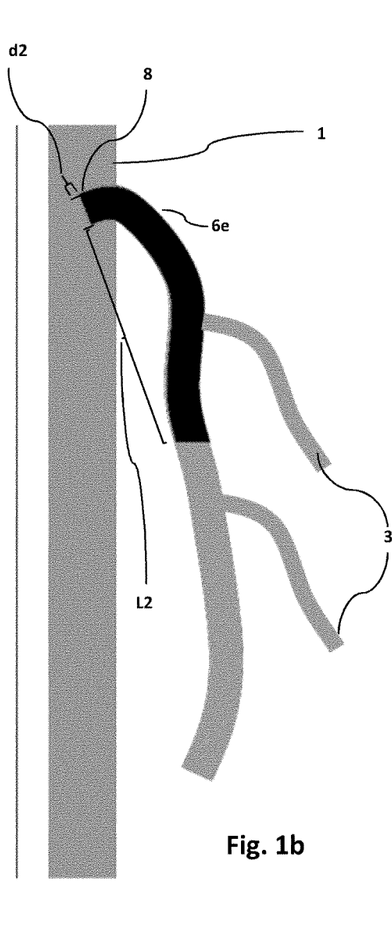
FIG. 1b: schematically the concept of a sectional treatment with one section.

FIG. 1b shows a vein system with a vein 1, and an insufficient vein 2 fed by smaller veins 3. According to the embodiment of the invention shown in FIG. 1b, only one section 6e of the vein 2 is treated.

Here, the refluxing vein 2 is the Great Saphenous Vein (GSV) (or alternatively the Anterior Accessory Saphenous Vein (AASV)). The treated section begins as close as possible to the sapheno-femoral junction 8, preferably at a distance d2 smaller than 2 cm. The length L2 of the treated section is larger than 5 cm, most preferably larger than 10 cm, but does not reach the level of the knee (not shown in FIG. 1b).

FIGS. 2a-2e show several other embodiments of the method according to the invention where the vein 2 to be treated has several tributaries 3.

Figure 2A:
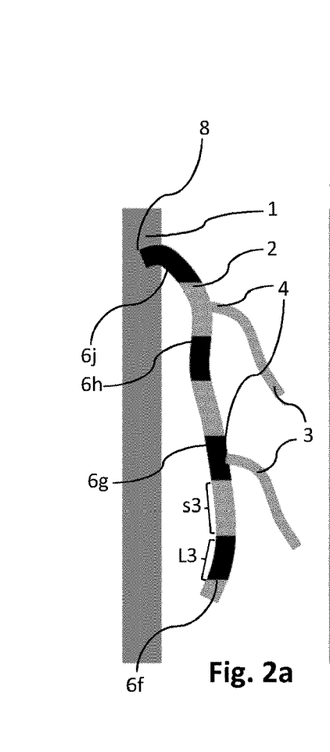
FIG. 2a: schematically the treatment of a vein without particularly adjusting the sections with respect to the tributaries.

In FIG. 2a, a treatment of a refluxing vein 2 with several tributaries 3 is schematically shown. The sectional treatment approach is applied independently from the location of the tributaries 3, but the treatment is begun at the sapheno-femoral junction 8. The sections 6f, 6g, 6h, and 6j are spread uniformly along the treated vein 2 and are adapted in the lengths L3 and spacing s3 irrespective of the position of the tributaries 3. Thus, in this particular embodiment, section 6g is located at a junction 4 between the refluxing vein 2 and a tributary 3, while the other sections 6f, 6h, and 6j are not. In this embodiment, only the vein 2 is treated even if a section 6g lies at a junction 4, meaning that the tributary 3 is not treated.

Figure 2B:
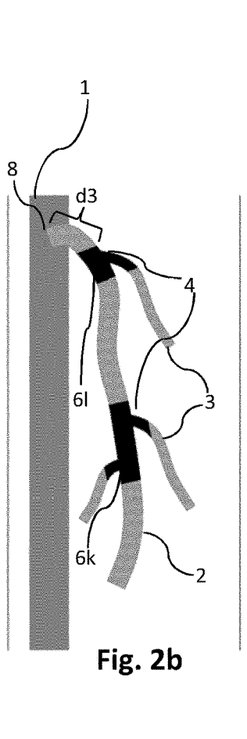
FIG. 2b: schematically a sectional treatment of a vein wherein both the vein and the tributaries are treated.

FIG. 2b shows schematically an embodiment of the method according to the invention, where sections 6k and 6l are placed to target the junctions 4 with the tributaries 3. This allows for avoiding a recanalization due to the blood inflow or a bypass of the treated sections which would transmit the increased pressure to the bottom of the leg. Both the vein 2 and the tributaries 3 are treated in the junction areas 4. Furthermore, in the shown embodiment, the sections have a length, spacing, and placement irrespective of the distance d3 to the sapheno-femoral junction 8 and the vein 1. However, the sections 6k, 6l are located such that they coincide with the junctions 4 and are thus not necessarily spread uniformly along the treated vein 2.

Figures 2C, 2D:
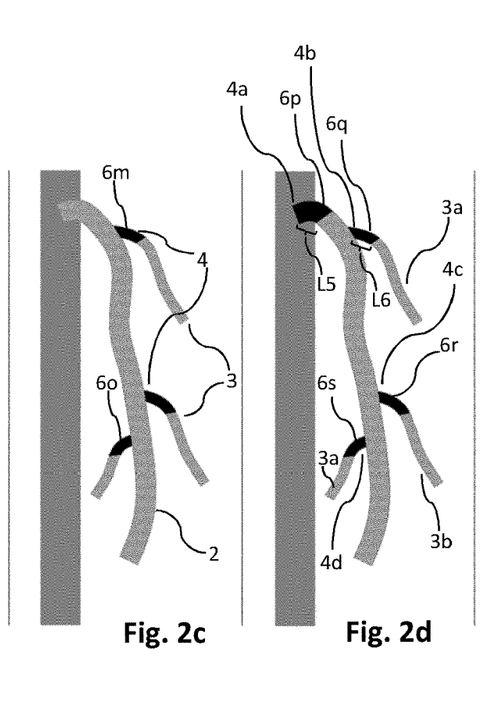
FIG. 2c: schematically a sectional treatment of a vein wherein only the tributaries are treated.
FIG. 2d: schematically a sectional treatment of a vein wherein only the tributaries are treated at the junctions.

FIG. 2c shows schematically another embodiment of the method according to the invention where only the tributaries 3 close to the junctions 4 are treated. The sections 6m and 6n lie on the tributaries 3, while the refluxing vein 2 itself is not treated.

FIG. 2d shows schematically an embodiment of the method according to the invention, where at each junction area 4a, 4b, 4c, and 4d, only the tributary portion of the junction is treated. As such, only the part of the refluxing vein 2 that is directly adjacent to the vein 1 is treated and section 6p is placed accordingly. Similarly, the sections 6q, 6r, and 6s are placed such that the tributaries 3a, 3b, and 3c are treated at the junction area 4b, 4c, and 4d where they are connected to the refluxing vein 2. In contrast to FIG. 2c, the refluxing vein 2 is also treated with a section 6p at the junction 4a between the vein 1 and the refluxing vein.

FIG. 2d corresponds to a preferred method of treatment of a GSV or an AASV. This embodiment includes treatment of at least one section at the sapheno-femoral junction 8 and occlusion of some of, preferably all, the tributaries 3 upstream to or at the junctions with the GSV or AASV.

Preferably, the length 15 of the treated section 6p at the sapheno-femoral junction 8 is larger and/or the delivered energy is higher, and/or the linear endovenous energy density is higher for the other sections 6q, 6r, and 6s.

Similarly, if a tributary 3a is larger than the other tributaries 3b and 3c, the length L6 of the treated section 6q at the junction 4b is preferably larger and/or the delivered energy is preferably higher, and/or the linear endovenous energy density is preferably higher than for the sections 6r and 6s at the sections 4c and 4d.

Figure 2E:
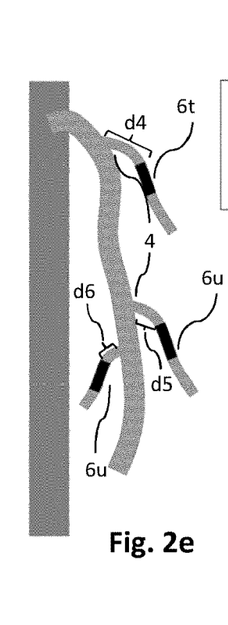
FIG. 2e: schematically a sectional treatment of a vein wherein only the tributaries are treated.

FIG. 2e schematically shows another preferred embodiment of the method according to the invention, wherein only the tributaries 3 are treated. The sections 6t, 6u, and 6v are located at a distance d4, d5, and d6, from the junction areas 4, respectively.

Figure 3:
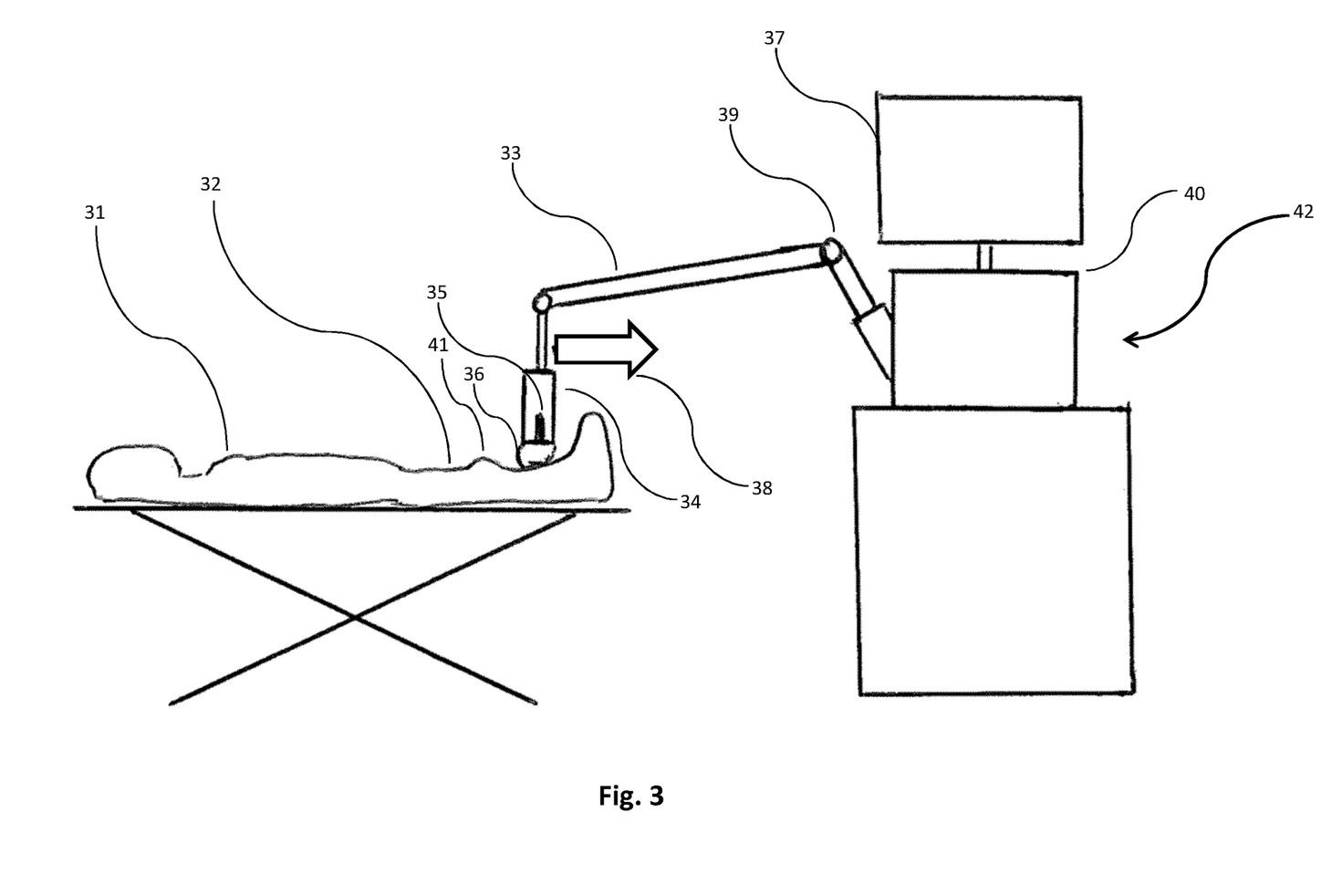
FIG. 3: schematically a device for carrying out the present invention.

FIG. 3 shows schematically a device 42 which can be used to perform the method according to the invention, wherein a patient 31 is treated by HIFU. The device comprises a treatment head 34 which is placed on the patient's leg 32 below his knee 41. Here, some of the treated sections lie in the calf and thus, some areas below the knee are treated. It is possible, however, to only treat sections in the thigh. In this particular embodiment of the device, the treatment head 34 comprises a balloon 36 that is in contact with the patient's leg 32 and enables acoustic coupling. The treatment head 34 comprises a transducer 35 for emitting ultrasound waves. A control unit 40 controls the emission of HIFU pulses. A memory unit (not shown) saves the number of sections and at least some of the treatment characteristics for each section. In this exemplary embodiment, the memory unit saves the number of sections that were treated along with their location and pulse power, pulse length, and the number of pulses. In this particular case, other treatment characteristics are not of interest, but it is clear to a person skilled in the art that the memory may also save other treatment characteristics as required. The treatment head 34 is connected to the control unit 40 through a robotic arm 33. The arm 33 comprises mechanical joints 39 in order to perform a controlled movement 38 of the arm. In this embodiment, the device comprises a user interface in the form of a display 37. The display displays to a user the treatment characteristics that were saved in the memory. Here, this happens in the form of a schematic diagram which shows the location of the sections on a dedicated part of the screen. In addition, the control unit also computes the average pulse power and the standard deviation, which is classified into ranges associated to a color. The different sections on the displays are thus colored, wherein each color represents a pulse power range. The other treatments characteristics are displays as alphanumerical digits on the display. They may, however, also be displayed symbolically by, for example, a number of dots in the sections, the thickness of a line, or others.

Treatment parameters for the sections Include, but are not limited to, frequency, number of pulses, energy, pulse spacing, duration, LEED (W/cm), and fluence (W/cm²).

Figure 4:
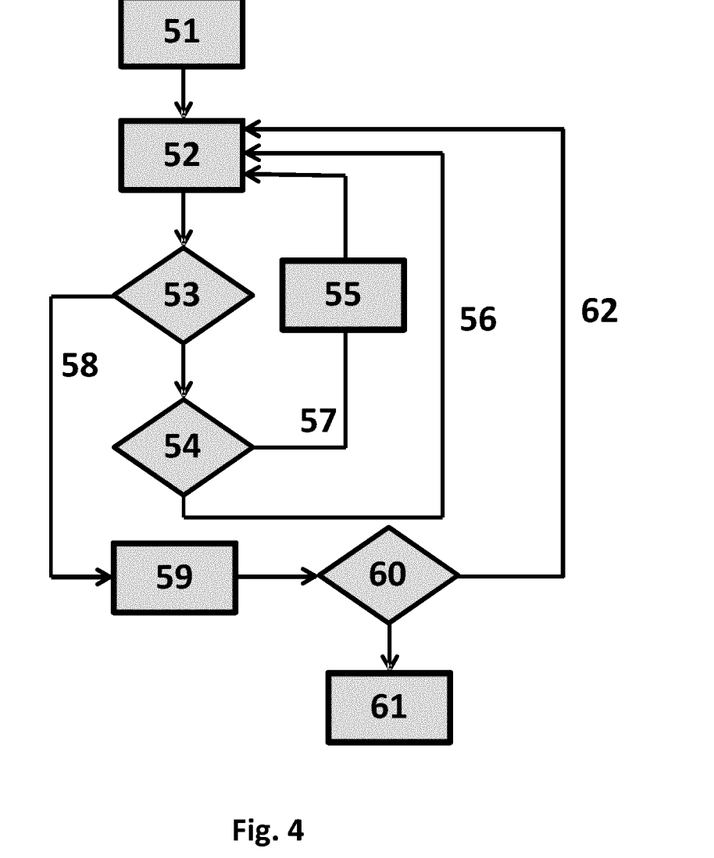
FIG. 4: schematically by means of a flow chart the steps of a method according to the invention.

FIG. 4 shows schematically, by way of a flow chart, the steps of a method according to the invention. In a first step 51, a section to be treated is identified and the treatment parameters are determined. Here, the treatment parameters include the frequency, number of pulses, and total delivered energy for all sections to be treated. Other parameters can be included in addition or as an alternative to the parameters used here. A treatment step 52, comprising the emission of a HIFU pulses with the pre-determined frequency is performed subsequently without moving the treatment head. Alternatively, multiple HIFU pulses can be emitted in one treatment step. A further step consists in comparing the treatment with a pre-determined stopping condition 58. Here, the treatment a section shall be terminated upon delivery of a total amount of energy. Alternatively, stopping parameters could total number of HIFU pulses, total length of the treated section, duration of the treatment, and others. If the condition for stopping 53 is not met, the visibility of the treated vein is checked 54. If is well visible 56, the treatment is continued by performing another treatment step 52. If the vein is not visible 57, the treatment head is moved, preferably distally, in a movement step 55, for example to treat another section. Subsequently, the treatment is continued with another treatment step 52. If and when the stopping condition 53 is met 58, the treatment of section is stopped 59. If another section is planned to be treated 60, the procedure is repeated 62 with another treatment step 52 for the new section. In this embodiment, the treatment parameters are pre-defined for the next section and another planning and identifying step 51 can be omitted. However, it would also be possible to identify a section and/or determine the treatment parameters after a section has already been treated. If no new section is to be treated, the procedure is finished 61.

Figure 5A:
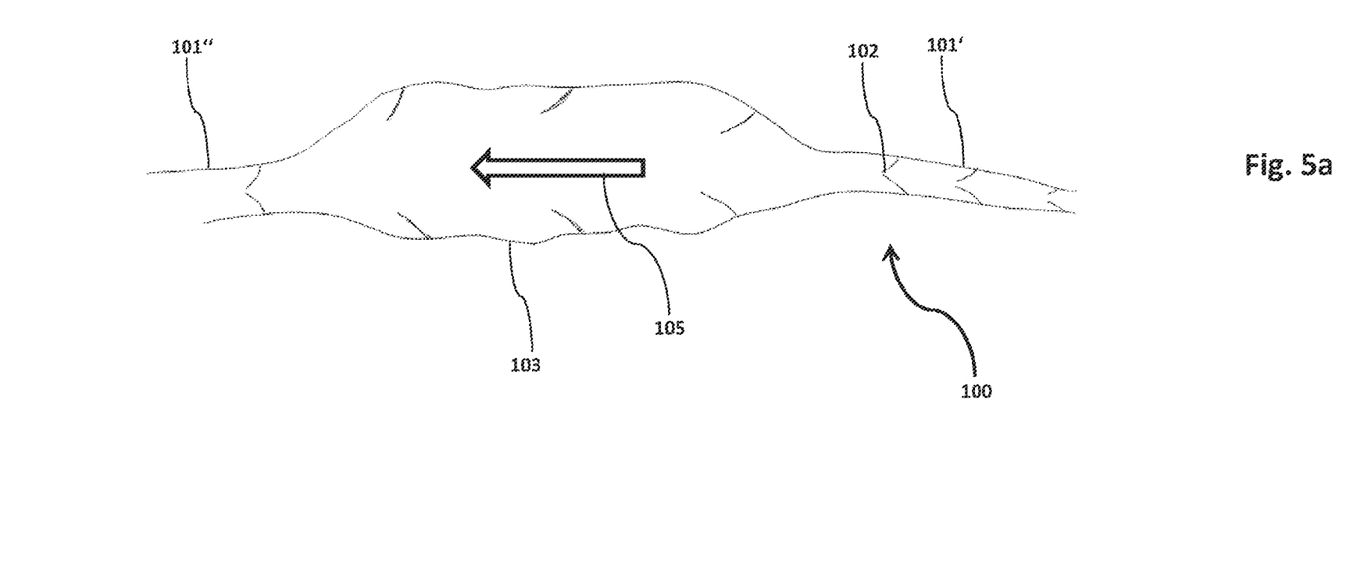
FIGS. 5a-5b: a detailed view of a sectional treatment.

FIG. 5a shows schematically a varicose vein 100 before a treatment. In healthy parts of the vein 101',101", the vein 100 comprises valves 102 that are functional and prevent the flow of blood in a direction opposite the natural direction of flow 105 of blood. The vein 100 has a varicose segment 103 where a diameter of the vein is extended and the vein 100 dilated. The valves 105 do not close in the varicose segment 103. Therefore, blood may flow against the normal direction 105.

Figure 5B:
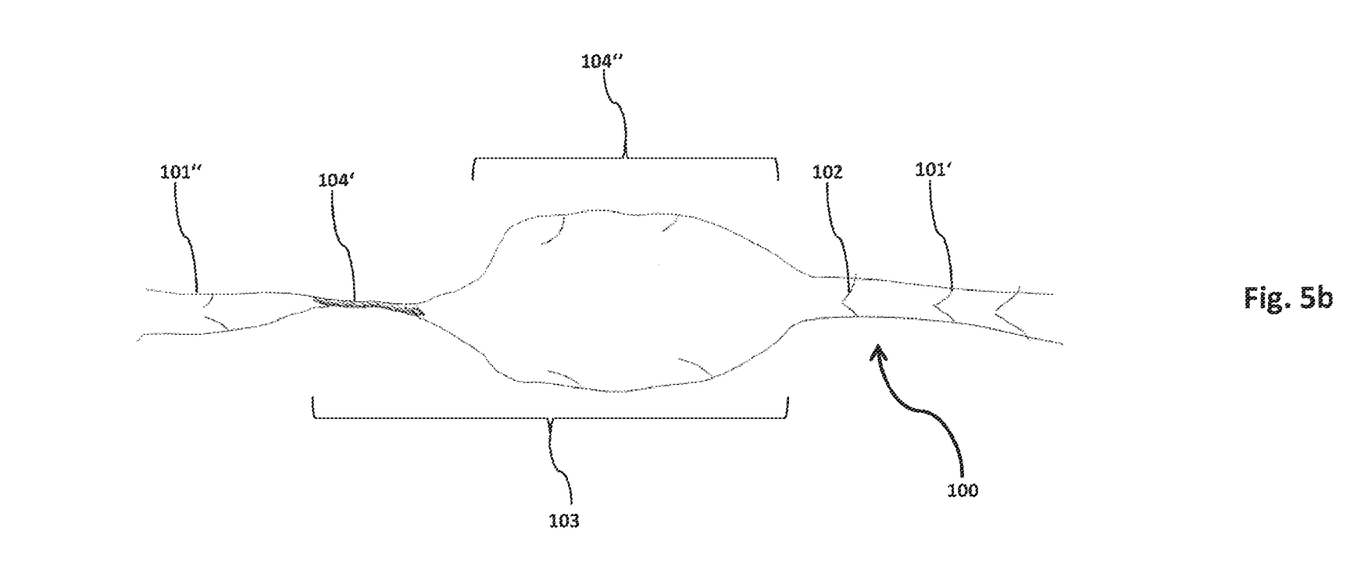

FIG. 5b schematically shows the vein 100 after a treatment according the invention. A section 104' at a distal end, i.e. at a downstream end of the segment 103, has been treated with HIFU and is completely occluded as a result. A second section 104" adjacent to the first section 104' is untreated. The occlusion of first section 104' is sufficient to restore the functionality of the vein system. Additionally, it would be possible to treat at least a part of the second section 104" with a sclerosant.

The invention claimed is:

1. A method of treating varicose veins by application of high intensity focused ultrasound (HIFU), the method comprising the steps of:
    identifying a larger segment of a vein which is non-functional, the larger segment of the vein which is non-functional having a plurality of sections including at least one first non-functioning section and at least one second non-functioning section, and identifying the at least one first non-functioning section of the segment of the vein which is to be treated; and
    treating the at least one first non-functioning section to be treated by applying high-intensity focused ultrasound (HIFU) emitted from a treatment head to the at least one first non-functioning section without treating the at least one second non-functioning section, of the plurality of sections neighboring the at least one first non-functioning section to be treated, with the high-intensity focused ultrasound (HIFU)
    wherein at least one of a number, a length, a location, a characteristic LEED value, a treatment power, and/or a fluence of the first non-functioning section is defined, based on ultrasound imaging data, prior to the step of treating the first non-functioning section
    the at least one first non-functioning section to be treated is treated so as to occlude the at least one first non-functioning section.

2. The method according to claim 1, wherein the at least one first non-functioning section to be treated is treated without moving the treatment head.

3. The method according to claim 1, wherein at least two first non-functioning sections to be treated, which are spaced apart from one another by the at least one second non-functioning section which is located therebetween.

4. The method according to claim 1, wherein selecting the vein to be treated to be one of a Great Saphenous Vein or an Anterior Accessory Saphenous Vein, and the at least one first non-functioning section to be treated begins adjacent to a sapheno-femoral junction.

5. The method according to claim 4, wherein selecting a length of the at least one first non-functioning section to be treated to be longer than 5 cm.

6. The method according to claim 4, wherein a length of the at least one first non-functioning section to be treated is chosen so as not to reach a level of the knee.

7. The method according to claim 1, wherein selecting the vein to be treated to be a perforator vein, and the at least one first non-functioning section to be treated is located adjacent to a fascia.

8. The method according to claim 3, wherein at least one of a length and a spacing of the at least two first non-functioning sections to be treated is chosen such that sensitive structures, such as nerves present along the vein, are not subject to the high-intensity focused ultrasound (HIFU).

9. The method according to claim 3, wherein selecting the vein to be treated to extend at least one of in a thigh and in a calf of the patient.

10. The method according to claim 3, wherein more than one first non-functioning section to be treated is selected from the plurality of sections, and a number, a length and a location of each of the first non-functioning sections to be treated, is defined prior the treatment.

11. The method according to claim 3, wherein more than the at least one first non-functioning section to be treated is selected from the plurality of sections, wherein a number, a length and a location of the sections to be treated, is adjusted during the treatment.

12. The method according to claim 11, wherein the length of the at least one first non-functioning section to be treated is reduced during the treatment in dependence of a reduced visibility of the treated vein, and the treatment head is moved distally in dependence of the reduced visibility of the vein and a new section is treated at a more distal location.

13. The method according to claim 1, wherein treatment is controlled on the basis of at least one of a level of total delivered energy, absence of detectable flow in the vein, a treatment duration, a total treated length, a vein shrinkage, and a predefined number of sections treated.

14. The method according to claim 3, wherein the at least two first non-functioning sections to be treated are treated from a proximal side of the vein to a distal side of the vein.

15. The method according to claim 3, wherein the treatment is started with a distal-most section.

16. The method according to claim 3, wherein the at least one first non-functioning section to be treated is placed to target a junction with a tributary.

17. The method according to claim 16, wherein an occlusion of a junction includes one of: (i) treating only the vein at said junction, (ii) treating the vein and a tributary at said junction and (iii) treating only the tributary at the junction.

18. A method of treating varicose veins by application of high intensity focused ultrasound (HIFU), the method comprising the steps of:
identifying a larger segment of a vein which is non-functional, the larger segment of the vein which is non-functional having a plurality of sections including at least one first and one third non-functioning section and at least one second non-functioning section, and identifying the at least one first and the at least one third non-functioning section of the segment of the vein which is to be treated; wherein the first non-functioning section and third non-functioning section are spaced apart from one another by the at least one second non-functioning section which is located therebetween and
treating the at least one first and the at least one third non-functioning section to be treated by applying high-intensity focused ultrasound (HIFU) emitted from a treatment head to the at least one first non-functioning section without treating the at least one second non-functioning section, of the plurality of sections neighboring the at least one first non-functioning section to be treated, with the high-intensity focused ultrasound (HIFU)
the at least one first non-functioning section to be treated is treated so as to occlude the at least one first non-functioning section.

19. A method of treating varicose veins by application of high intensity focused ultrasound (HIFU), the method comprising the steps of:
identifying a larger segment of a vein which is non-functional, the larger segment of the vein which is non-functional having a plurality of sections including at least one first non-functioning section and at least one second non-functioning section, and identifying the at least one first non-functioning section of the segment of the vein which is to be treated; and
treating, so as to occlude, the at least one first non-functioning section to be treated by applying high-intensity focused ultrasound (HIFU) emitted from a treatment head to the at least one first non-functioning section without treating the at least one second non-functioning section, of the plurality of sections neighboring the at least one first non-functioning section to be treated, with the high-intensity focused ultrasound (HIFU),
wherein selecting the vein to be treated to be one of a Great Saphenous Vein, an Anterior Accessory Saphenous Vein, and a perforator vein, and further wherein
the at least one first non-functioning section to be treated begins either, if the vein to be treated is the Great Saphenous Vein or the Anterior Accessory Saphenous Vein, adjacent to a sapheno-femoral junction, or, if the vein to be treated is the perforator vein, adjacent to a fascia
the at least one first non-functioning section to be treated is treated so as to occlude the at least one first non-functioning section.

20. The method according to claim 19, further comprising a step of treating at least a part of a same vein system using sclerotherapy.

21. The method according to claim 18, wherein selecting the vein to be treated to be one of a Great Saphenous Vein or an Anterior Accessory Saphenous Vein, and the at least one first non-functioning section to be treated begins adjacent to a sapheno-femoral junction.

22. The method according to claim 18, wherein at least one of a length and a spacing of the at least first and third non-functioning sections to be treated is chosen such that sensitive structures, such as nerves present along the vein, are not subject to the high-intensity focused ultrasound (HIFU).

23. The method according to claim 18, wherein treatment is controlled on the basis of at least one of a level of total delivered energy, absence of detectable flow in the vein, a treatment duration, a total treated length, a vein shrinkage, and a predefined number of sections treated.

24. The method according to claim 18, wherein the at least first and third non-functioning sections to be treated are treated from a proximal side of the vein to a distal side of the vein.

25. The method according to claim 18, wherein the treatment is started with a distal-most section.

26. The method according to claim 18, wherein the at least one first non-functioning section to be treated is placed to target a junction with a tributary, and wherein an occlusion of a junction includes one of: (i) treating only the vein at said junction, (ii) treating the vein and a tributary at said junction and (iii) treating only the tributary at the junction.

27. The method according to claim 18, wherein the at least first non-functioning section and third non-functioning section are arranged in a regular pattern.

\* \* \* \* \*